United States Patent [19]

Barone et al.

[11] Patent Number: 4,565,880

[45] Date of Patent: Jan. 21, 1986

[54] MALEIC ANHYDRIDE PROCESS

[75] Inventors: Bruno J. Barone, Houston; William G. Bowman, Dickinson, both of Tex.

[73] Assignee: Denka Chemical Corporation, Houston, Tex.

[21] Appl. No.: 508,870

[22] Filed: Jun. 29, 1983

[51] Int. Cl.$^4$ .............................................. C07D 307/60
[52] U.S. Cl. .................................... 549/256; 549/262
[58] Field of Search ................................ 549/262, 256

[56] References Cited

U.S. PATENT DOCUMENTS 2,134,531 10/1938 Punnett ................................. 549/262
2,343,536 3/1944 Crowell ................................. 549/262
2,509,873 5/1950 McAteer ............................... 549/262
2,863,880 12/1958 Kohn ..................................... 549/262

Primary Examiner—Henry H. Jiles
Assistant Examiner—Bernard I. Dentz
Attorney, Agent, or Firm—Kenneth H. Johnson

[57] ABSTRACT

It has been found that phosphoric acid alone and in admixture with phenothiazine and/or methyl-p-benzoquinone reduces residue formed during the fractionation of aqueous crude maleic compositions for the production of maleic anhydride, and in particular, reduces residue due to the presence of small amounts, i.e., less than 10 ppm alkali metal ion. When the alkali metal ion is present at least 9 equivalent acid groups of phosphoric acid per atomic equivalent of alkali metal ion are present.

20 Claims, No Drawings

MALEIC ANHYDRIDE PROCESS

BACKGROUND OF THE INVENTION

1. Field of the Invention

The present invention relates to an improvement in the process of producing maleic anhydride where a water scrubber is employed, by adding a stabilizing material to the scrubber water to reduce residue formation and loss of maleic anhydride during distillation separation of the water from the crude maleic composition.

2. Related Art

Maleic anhydride is currently produced by the oxidation of hydrocarbons such as benzene, n-butene, butadiene-1,3 or n-butane. Maleic anhydride is obtained by oxidizing the hydrocarbon feed at a high temperature and over a suitable catalyst to produce a gaseous effluent of maleic anhydride together with impurities. The gaseous effluent is cooled and scrubbed with water to produce a crude solution of maleic acid. The aqueous solution of maleic acid is then fed to a dehydration-distillation column in which the maleic acid is dehydrated by contacting with a volatile water insoluble entraining or azeotroping agent such as xylene which does not undergo chemical reaction in the system. The water and entraining agent are removed as overhead vapors and maleic anhydride is removed as bottoms. These processes for the oxidation of hydrocarbons to maleic anhydride, scrubbing of the maleic anhydride to produce an aqueous maleic acid solution and dehydration of the maleic acid solution to form maleic anhydride are known in the art and are described, for example, in Chemical and Engineering News 38, (28), 40, 1960; Encyclopedia of Polymer Science (1964); Kirk and Othmer Encyclopedia of Chemical Technology, 2nd. edition, Vol. 12, 828, Interscience (1967); U.S. Pat. No. 2,683,110 and U.S. Pat. No. 3,094,539. One of the disadvantages of these methods of dehydration is that a significant amount of maleic anhydride is lost as residue which is believed to be primarily fumaric acid and a conglomeration of higher molecular weight substances formed during the dehydration. The residue also produces fouling in the dehydration column.

The presence of sodium in the crude product is known to promote the rate of maleic anhydride decomposition and residue formation at elevated temperatures. Sodium may be introduced into the system with scrubber water makeup. U.S. Pat. No. 2,863,880 issued to Kohn found that phosphoric acid inhibited the alkali metal-induced decomposition of maleic anhydride, however, Kohn was dealing with what are considered relatively high amounts of alkali, i.e., 50 ppm or more. Moreover, Kohn stated that about six to eight equivalent acid groups per atomic equivalent of alkali metal ion was the maximum amount required to inhibit the system and that no advantage was observed for increased quantities.

That may be the case with large amounts of alkali metal, e.g., sodium, however, plants now generally operate with water of greater purity, with alkali content of 10 ppm or less. Surprisingly, it has been found for these low concentrations of alkali, much larger amounts of phosphoric acid are required to inhibit the alkali and the resultant residue formation.

Although, alkali ions are a major cause of maleic anhydride degradation during the dehydration, there are other factors, which cause residue. These other factors have not been identified. However, the use of phosphoric acid according to the present invention also reduces the residue formation of alkali free maleic anhydride due to these other factors.

It has also been found that a combination of phosphoric acid with certain other compositions provides a synergistic effect in the residue formation.

SUMMARY OF THE INVENTION

Simply stated, the present invention is the process of producing maleic anhydride comprising (1) oxidizing a hydrocarbon which is a precursor of maleic anhydride to form a reactor effluent comprising maleic anyhdride (2) scrubbing the reactor effluent with water to obtain a crude aqueous composition comprising maleic acid and up to 10 ppm of an alkali metal ion (3) recovering the maleic product by fractionation of said crude aqueous composition wherein the improvement comprises having present in said aqueous composition, phosphoric acid in the range of from about 100 to 2000 parts per million (ppm) and in a ratio of at least 9 equivalent acid groups per atomic equivalent of alkali metal ion present or a combination of said phosphoric acid and from 10 to 150 ppm phenothiazine, methyl-p-benzoquinone or a mixture thereof whereby the loss of said maleic anhydride by residue formation is reduced.

The residue is believed to be formed primarily by degradation, polmerization and/or isomerization of the maleic anhydride.

The minimum amount of phosphoric acid OH equivalents per atomic equivalent of alkali metal ion has been determined to be 9, and a maximum of 140 is preferred. Although some benefit would appear to be gained by larger ratios of phosphoric acid OH equivalents, the slight incremental increase would not justify higher ratios in commercial utilization.

DETAILED DESCRIPTION OF THE INVENTION

The crude maleic anhydride can be obtained by oxidation of hydrocarbons as is known in the art. The feed may be e.g., benzene, n-butene, butadiene-1,3, n-butane and mixtures thereof. The reactor effluent is then scrubbed with water to form the aqueous maleic acid composition. It is possible to condense a portion of the maleic anhydride prior to scrubbing. This scrubbing or contact of the reactor effluent may be accomplished in any conventional manner, and conventional equipment for gas/liquid mixing may be used such as scrubbers, turbo-absorbers, bubble or tray towers, absorbers, cascades, injector systems for recirculation through nozzles or towers and the like. Conventional equipment used for the scrubbing of maleic acid may be employed. At atmospheric pressure typical temperatures of the water will be about 20° C. to 90° C. with a preferred range being about 40° C. to 60° C. Both higher and lower temperatures may be used.

The product discharge from the water scrubber contains at least 40 weight percent water and preferably contains about 30 to 60 weight percent of maleic acid, with a preferred range being from about 35–45 weight percent maleic acid. The resultant maleic acid solution will generally contain impurities such as fumaric acid, benzene derivatives, formaldehyde and related impurities depending upon the particular hydrocarbon fed to the reactor. Weak acids such as aliphatic monocarboxylic acids of 2 to 6 carbon atoms may be present. Aliphatic aldehydes of 2 to 6 carbon atoms may be present and there may be a variety of mixed tarry polymers such as from about 0.05 to 5 weight percent of the maleic acid.

The maleic acid composition may be dehydrated and recovered according to this invention. If desired, the scrubber water may be pretreated to adjust for temperature or pressure or to remove certain impurities. However, it is one of the advantages of this invention that the maleic acid scrubber water can be conducted directly to the dehydration and recovery process. In the dehydration process the maleic acid solution is at a temperature at least as high as the boiling point of the aqueous composition and it is essential that water or a water azeotrope be boiled off. The boiling points of course will be influenced by the pressure under which dehydration takes place. A preferred method of conducting the invention is to continously feed maleic acid composition containing the phosphoric acid and other components to a distillation column. Preferably, the maleic acid composition will be fed to the upper two-thirds of the column but at a point below the very top of the column, for example, not on the top plate if a plate column is used. The aqueous maleic acid composition may be fed to the stillpot but generally better results are obtained if the maleic acid composition is fed in the middle one-third of the distillation column. In the distillation column a water or water azeotrope comes off overhead and this may be separated by cooling in a condenser and decanting with the azeotroping agent being recycled to the column and the water from the decanter being discharged to an appropriate treatment pond.

Continuously removing the product from a stillpot is an alternate method to operate the process as a batch process followed by separation of the product at the end of the process. Combinations of continuous and batch process techniques may be employed.

The dehydration column may be a fractionation tower such as a sieve plate, bubble cap or packed tower. Conventional equipment used for the dehydration of maleic acid compositions may be employed.

Although the alkali metals all exhibit a detrimental effect on the maleic anhydride, sodium ion is of primary concern, since it is present in such relatively large quantities in much of the water used for scrubbing, and hence can not be removed to negligable levels. A typical scrubber water for use in a plant operation having as low as 1 ppm sodium ion content will still exhibit a degrading effect on the maleic anhydride production which can be reduced according to the present invention. The lowest level of sodium ion concentration that will have an adverse effect has not been determined, since maleic anhydride which is free of sodium (alkali) ion to the degree of sensitivity of the analytical method (0.1 ppm) still exhibits some residue production during dehydration. Generally in the present process alkali metal ion will be present in an amount up to 5 ppm and usually from about 0.5 ppm.

The pressure in the dehydration reaction may be varied and may be sub-atmospheric, atmospheric, or above atmospheric pressure. According to one method of operation the dehydration can be conducted at about atmospheric pressure and thereafter the pressure in the stillpot and the column can be increased to greater than atmospheric pressure, such as from 25 to 100 psig, to drive the separation to completion. The temperature in the stillpot and in the overhead from the dehydration column will vary depending upon the particular compositions of water and for entraining agent (azetroping agent) being employed but the temperature of the overhead from the column must be at least as high as the boiling point of the aqueous maleic composition being dehydrated under the particular pressure conditions. Preferably during dehydration the temperature in the stillpot will be between 100° and 230° C. The overhead temperature may be varied depending on the pressure and the components used but normally will be between about 80° and 200° C.

In addition to water, a water insoluble entraining agent (or azeotroping liquid) may be present. The entraining agent forms an azeotrope with the water and thereby improves removal of water and some impurities. The exact nature of the impurities is not known. The azeotroping liquid functions to remove the maleic acid dilution water, to dehydrate the maleic acid to maleic anhydride and to purify the maleic anhydride. The maleic anhydride plus some azeotroping liquid comes off as bottoms from the dehydration column.

Various azeotroping liquids may be selected. Water and maleic anhydride may or may not be miscible with the azeotroping liquid. If the azeotroping liquid is miscible with the anhydride, then it should have a lower boiling point than maleic anhydride in order that it might be separated by distillation from the anyhydride. The azeotroping liquid may be, for example, the ortho, meta or paraxylenes, mixed xylenes, toluene, benzene, petroleum naphtha, chlorobenzene, ethyl benzene, dipropyl ketone, mixtures thereof and the like. Normally, the boiling point of the azeotroping liquid will be from about 130° to 180° C.

The maleic product will be present in the stillpot for further purification or use.

In the following examples the effectiveness of the stabilizing compositions was determined by the amount of decrease in residue compared to a control. The following examples illustrate the invention, but are not intended to limit the scope thereof.

EXAMPLES 1-9

In these examples 10 ppm sodium ion (as sodium maleate) was added to each test sample and different levels of phosphoric acid added. The effectiveness of the additive is measured by the percent of residue reduction. Two controls free of sodium and additive were averaged to provide the basis for comparison. 50 gram samples of molten anhydride was added to a tared 100 ml pear shaped 2-neck flask. Prior to the anhydride addition, the inhibitor was added. Liquid materials were weighed directly into the flask. Solid materials were weighed separately. The flask was fitted with an air-cooled condenser and thermometer, and heated just sufficiently to reflux the anhydride at atmospheric pressure, the temperature was 205° C. and was continued for 6 hours.

After the 6 hour heating period, the anhydride was vacuum distilled in the same flask fitted with a Claison type head, non-fluxing condenser and receiver. The pressure was adjusted so that the maleic anhydride distilled overhead at approximately 120° C. $N_2$ gas was sparged below the liquid to prevent bumping and also to obtain complete recovery of anhydride at the end of the distillation. The internal flask temperature was not allowed to exceed 190° C. The heating mantle was adjusted so that the outer surface of the flask did not exceed 425° C. The results at various concentrations of phosphoric acid are set forth in Table I.

In TABLE I the ratio of OH equivalents: Na ion was was determined as follows:

The OH gram equivalency of $H_3PO_4$ is $$\tfrac{1}{3} \text{ the formular weight} = \frac{98}{3} = 32.67$$

$$\text{Equivalent wt. of Na maleate} = \frac{160}{2} = 80$$

$$\text{Ratio} = \frac{\text{Wt. of 85\% } H_3PO_4 \times .85 \times 80}{\text{Wt. Na maleate} \times 32.67}$$

And the percentage reduction of residue was determined by:

$$\text{The reduction of residue} = \frac{3.92 - \text{wt. \% residue}}{3.92} \times 100$$

EXAMPLES 10–15

In these examples 5 ppm of sodium ion (as sodium maleate) was added to maleic anhydride, using the procedure described for examples 1–9. Examples 14 and 15 were averaged to provide the control to determine the percentage of the residue reduction. The results are set out TABLE II. It can be seen by comparing the results in TABLES I and II that at the same level of phosphoric acid concentration the percentage of residue reduction is lower for the 5 ppm Na contaminated samples, whereas one would expect a greater effectiveness.

In TABLE II the ratio of OH equivalent to sodium ion is calculated as follows:

$$\text{Ratio} = \frac{\text{Wt. of 85\% } H_3PO_4 \times 80 \times .85}{\text{Wt. Na maleate} \times 32.67}$$

And the % residual reduction as follows:

$$\text{\% Residue Reduction} = \frac{2.72 - \text{wt. \% residue}}{2.72} \times 100$$

EXAMPLES 16–17

These examples demonstrate that residue formation, which may result from other causes than sodium ion, is also inhibited, i.e., reduced by the presence of phosphoric acid. The maleic anhydride used in these examples was free of sodium ion contamination. The same procedure as described for examples 1–9 was used. The results are set out in TABLE III.

EXAMPLES 18–19

The effect of phosphoric acid added to the feed to a dehydrating column (continuous operation) was measured at two levels. The average sodium ion concentration present in the feed to the dehydrating column was 1.2 ppm. The improvement in the refining yield as a result of the phosphoric acid addition is shown in TABLE IV.

EXAMPLES 20–30

In these examples the effect of various inhibitors on maleic anhydride containing 10 ppm sodium is shown and the synergistic effect when the best of these are combined with $H_3PO_4$. In addition to the zero level Na control, example 6 is set out to show the improvement of 170 ppm phosphoric acid and 130 ppm of the second inhibitor over 502 ppm phosphoric acid alone. The same procedure as described above, for example 1–9 was used in the evaluations. The conditions and results are set out in TABLE V.

TABLE I

Conditions: 50 gms Maleic Anhydride Containing 10 ppm Na ion refluxed 6 hrs at 205° C.

| Example | ppm 100% H3PO4 | Ratio OH Eq NA | Wt. % Residue | % Reduction of Residue |
|---|---|---|---|---|
| 1 | 14 | 1.0 | 3.99 | 0 |
| 2 | 29 | 1.9 | 3.08 | 22 |
| 3 | 40 | 2.8 | 2.45 | 38 |
| 4 | 97 | 7.0 | 2.07 | 47 |
| 5 | 153 | 11.0 | 1.86 | 53 |
| 6 | 502 | 36.1 | 1.69 | 57 |
| 7 | 1000 | 73.5 | 1.29 | 67 |
| 8 | — | — | 3.83 | — |
| 9 | — | — | 4.00 | — |
| Avg. 8 & 9 | — | — | 3.92 | — |

TABLE II

Conditions: 50 gms Maleic Anhydride, 5 ppm Na ion refluxed 6 hrs at 205° C.

| Example | ppm 100% H3PO4 | Ratio OH Eq Na | Wt. % Residue | % Reduction of Residue |
|---|---|---|---|---|
| 10 | 100 | 15 | 2.08 | 23 |
| 11 | 200 | 31 | 1.99 | 27 |
| 12 | 500 | 77 | 1.70 | 37 |
| 13 | 1000 | 156 | 1.27 | 53 |
| 14 | — | — | 2.60 | — |
| 15 | — | — | 2.82 | — |
| Avg. 14 and 15 | | | 2.72 | |

TABLE III

Conditions: 50 gms Maleic Anhydride refluxed at 205° C. for 6 hrs, no Na ion

| Example | Additive | Wt. Residue | Wt. % Residue | Residue Reduction |
|---|---|---|---|---|
| 16 | Control (No Additive) | .683 | 1.37 | — |
| 17 | 1000 ppm H3PO4 | .386 | .77 | 44 |

TABLE IV

| Example | PPM (100% H3PO4) | RATIO OH EQUIV. Na | DEHYDRATOR REFINING YIELD AVG. % |
|---|---|---|---|
| | 0 | 0 | 82.87 |
| 18 | 30.36 | 9 | 90.56 |
| 19 | 47.66 | 14 | 95.23 |

(1) Data based on an average sodium content of 1.2 ppm in the scrubber. Removal of water during dehydration would increase the sodium level to approximately 2.4 ppm in the maleic anhydride solution recovered.

TABLE V

| Example | Inhibitor | PPM | Residue Wt. % | Residue % Decrease |
|---|---|---|---|---|
| (A) 50 gms pure maleic anhydride containing 10 ppm sodium refluxed for 6 hrs. at 205° C. | | | | |
| 20 | None | 0 | 4.3 | — |
| 21 | PTZ(a) | 120 | 3.1 | 27.9 |
| 22 | Methyl-p-Benzoquinone | 120 | 3.2 | 25.6 |
| 23 | NPH(b) | 100 | 3.6 | 16.3 |
| 24 | TBC(c) | 120 | 3.5 | 18.6 |
| 25 | IONOL(d) | 100 | 3.7 | 14.0 |
| 26 | EDTA(e) | 120 | 4.7 | — |
| 27 | Pyrocatechol | 120 | 5.0 | — |
| 28 | Triethyl Thiophosphate | 140 | 5.2 | — |
| 29 | PTZ +85% H3PO4 | 130 170* | 1.1 | 74.4 |
| 6 | 85% H3PO4 | 502* | 1.69** | 57 |

TABLE V-continued

| Example | Inhibitor | PPM | Residue Wt. % | Residue % Decrease |
|---|---|---|---|---|
| | (B) Same as (A) without sodium. | | | |
| 30 | None | 0 | 3.2 | |
| 31 | 85% H3PO4 +PTZ | 170* 130 | 0.3 | 90.6 |

*Based on 100% H3PO4
**Control Examples 8 & 9 averaged 3.92 residue
(a) PTZ = Phenothiazine
(b) NPH = N—Nitrosophenyl hydroxyl amine (ammonium salt)
(c) TBC = tertiary Butyl catechol
(d) IONOL = Ditertiary butyl-p-creosol
(e) EDTA = Ethylene diamine tetra acetic acid

The invention claimed is:

1. In the process of producing maleic anhydride comprising:
   (a) oxidizing a hydrocarbon which is a precursor of maleic anhydride to form a reactor effluent comprising maleic anhydride,
   (b) scrubbing the reactor effluent with water to obtain a crude aqueous composition comprising maleic acid and up to 10 ppm of an alkali metal, and
   (c) recovering maleic anhydride by fractionation of said crude aqueous composition wherein the improvement comprises having present in said aqueous composition, a combination of phosphoric acid in the range of 100 to 2000 ppm and in a ratio of at least 9 equivalent acid groups of phosphoric acid per atomic equivalent of alkali metal ion present and from 10 to 150 ppm phenothiazine, methyl-p-benzoquinone, or a mixture thereof whereby the loss of said maleic anhydride is reduced.

2. The process according to claim 1 wherein a mixture of phosphoric acid and phenothiazine is present in said crude aqueous composition.

3. The process according to claim 1 wherein a mixture of phosphoric acid and methyl-p-benzoquinone is present in said crude aqueous composition.

4. The process according to claim 1 wherein a mixture of phosphoric acid, phenothiazene and methyl-p-benzoquinone is present in said crude aqueous maleic composition.

5. The process according to claim 1 wherein sodium ion is present.

6. The process according to claim 2 wherein sodium ion is present.

7. The process according to claim 3 wherein sodium ion is present.

8. The process according to claim 1 wherein up to 5 ppm alkali metal ion is present.

9. The process according to claim 8 wherein sodium ion is present.

10. The process according to claim 8 wherein from about 0.01 ppm alkali metal ion is present.

11. The process according to claim 10 wherein sodium ion is present.

12. The process according to claim 1 wherein an entraining agent is present in (c).

13. The process according to claim 1 wherein the loss of maleic anhydride is characterized by a reduction in residue formed during (c).

14. The process according to claim 1 wherein the ratio of equivalent acid groups of phosphoric acid per atomic equivalent of alkali metal ion present is in the range up to 140.

15. The process according to claim 1 wherein said crude aqueous composition contains from 30 to 60 weight % maleic acid.

16. The process according to claim 12 wherein said entraining agent has a boiling point in the range of 130° C. to 180° C.

17. In the process of producing maleic anhydride comprising:
   (a) oxidizing a hydrocarbon which is a precursor of maleic anhydride to form a reactor effluent comprising maleic anhydride,
   (b) scrubbing the reactor effluent with water to obtain a crude aqueous composition comprising maleic acid and up to 5 ppm of an alkali metal, and
   (c) recovering maleic anhydride by fractionation of said crude aqueous composition wherein the improvement comprises having present in said aqueous composition, phosphoric acid in the range of 100 to 2000 ppm and in a ratio of 15 to 156 equivalent acid groups of phosphoric acid per atomic equivalent of alkali metal ion present whereby the loss of said maleic anhydride is reduced.

18. The process according to claim 17 wherein sodium ion is present.

19. The process according to claim 17 wherein an entraining agent is present in (c).

20. The process according to claim 17 wherein the loss of maleic anhydride is characterized by a reduction in residue formed during (c).

* * * * *